(12) United States Patent
Yang et al.

(10) Patent No.: US 10,668,158 B2
(45) Date of Patent: Jun. 2, 2020

(54) SUSTAINED-RELEASE PREPARATION OF POORLY SOLUBLE DRUG

(71) Applicant: UNIVERSITY-INDUSTRY FOUNDATION, YONSEI UNIVERSITY, Seoul (KR)

(72) Inventors: Jaemoon Yang, Seoul (KR); Jin-Suck Suh, Seoul (KR); Young Han Lee, Seoul (KR); Dan Heo, Seoul (KR)

(73) Assignee: UNIVERSITY-INDUSTRY FOUNDATION, YONSEI UNIVERSITY, Seoul (KR)

(*) Notice: Subject to any disclaimer, the term of this patent is extended or adjusted under 35 U.S.C. 154(b) by 0 days.

(21) Appl. No.: 15/776,913

(22) PCT Filed: Feb. 26, 2016

(86) PCT No.: PCT/KR2016/001952
§ 371 (c)(1),
(2) Date: May 17, 2018

(87) PCT Pub. No.: WO2017/086545
PCT Pub. Date: May 26, 2017

(65) Prior Publication Data
US 2018/0326076 A1 Nov. 15, 2018

(30) Foreign Application Priority Data
Nov. 17, 2015 (KR) .................. 10-2015-0160885

(51) Int. Cl.
| | | |
|---|---|---|
| *A61K 47/36* | (2006.01) | |
| *A61K 31/5415* | (2006.01) | |
| *A61K 9/06* | (2006.01) | |
| *A61K 31/728* | (2006.01) | |
| *A61K 31/122* | (2006.01) | |
| *A61K 31/192* | (2006.01) | |
| *A61K 31/444* | (2006.01) | |
| *A61K 31/60* | (2006.01) | |
| *A61K 47/12* | (2006.01) | |
| *A61P 29/00* | (2006.01) | |
| *A61K 9/19* | (2006.01) | |
| *A61K 9/00* | (2006.01) | |
| *A61K 9/10* | (2006.01) | |
| *A61K 31/337* | (2006.01) | |
| *A61K 47/10* | (2017.01) | |
| *A61K 47/18* | (2017.01) | |
| *A61K 47/20* | (2006.01) | |
| *A61P 1/16* | (2006.01) | |
| *A61P 35/02* | (2006.01) | |
| *A61P 1/04* | (2006.01) | |

(52) U.S. Cl.
CPC ............ *A61K 47/36* (2013.01); *A61K 9/0019* (2013.01); *A61K 9/06* (2013.01); *A61K 9/10* (2013.01); *A61K 9/19* (2013.01); *A61K 31/122* (2013.01); *A61K 31/192* (2013.01); *A61K 31/337* (2013.01); *A61K 31/444* (2013.01); *A61K 31/5415* (2013.01); *A61K 31/60* (2013.01); *A61K 31/728* (2013.01); *A61K 47/10* (2013.01); *A61K 47/12* (2013.01); *A61K 47/18* (2013.01); *A61K 47/20* (2013.01); *A61P 1/04* (2018.01); *A61P 1/16* (2018.01); *A61P 29/00* (2018.01); *A61P 35/02* (2018.01)

(58) Field of Classification Search
CPC .. A61K 31/122; A61K 31/192; A61K 31/337; A61K 31/444; A61K 31/5415; A61K 31/60; A61K 9/0019; A61K 9/06; A61K 9/10; A61K 9/19; A61K 47/10; A61K 47/12; A61K 47/18; A61K 47/20; A61K 47/36; A61P 1/04; A61P 1/16; A61P 29/00; A61P 35/02
See application file for complete search history.

(56) References Cited

U.S. PATENT DOCUMENTS

| | | | | |
|---|---|---|---|---|
| 4,628,053 A | * | 12/1986 | Fries ................. | A61K 9/0019 514/226.5 |
| 5,756,450 A | | 5/1998 | Hahn et al. | |
| 6,491,953 B1 | * | 12/2002 | Sojka ................. | A61K 9/5015 424/400 |

(Continued)

FOREIGN PATENT DOCUMENTS

| | | |
|---|---|---|
| KR | 1994-0001891 | 2/1994 |
| KR | 10-0336090 | 5/2002 |

(Continued)

OTHER PUBLICATIONS

UCLA, Chemistry Dept., How to use a Rotary Evaporator, publ. online Apr. 1, 2010, http://www.chem.ucla.edu/~bacher/Specialtopics/rotavap.html (Year: 2010).*

(Continued)

*Primary Examiner* — Sarah Pihonak
(74) *Attorney, Agent, or Firm* — Meunier Carlin & Curfman LLC

(57) ABSTRACT

The present invention relates to a pharmaceutical composition containing a poorly soluble drug, hyaluronic acid, and a fatty acid, and to a method for preparing the same. The pharmaceutical composition of the present application has excellent stability even for long-term storage and allows a sustained release of the drug, thereby preventing an overdose of the drug and improving the therapeutic efficiency at an effected area.

6 Claims, 7 Drawing Sheets
(7 of 7 Drawing Sheet(s) Filed in Color)

(56) References Cited

U.S. PATENT DOCUMENTS

| | | | |
|---|---|---|---|
| 6,706,286 B1* | 3/2004 | Zagnoli | A61K 9/0056 424/464 |
| 2001/0005501 A1 | 6/2001 | Marriott et al. | |
| 2007/0036728 A1 | 2/2007 | Mohapatra et al. | |

FOREIGN PATENT DOCUMENTS

| | | | |
|---|---|---|---|
| KR | 10-2009-0040979 | 4/2009 | |
| WO | WO-0000179 A1 * | 1/2000 | A61K 9/145 |

OTHER PUBLICATIONS

English translation of International Search Report and Written Opinion dated Sep. 29, 2016, from International Application No. PCT/KR2016/001952, 11 pages, Sep. 29, 2016.

* cited by examiner

[FIG. 1A]
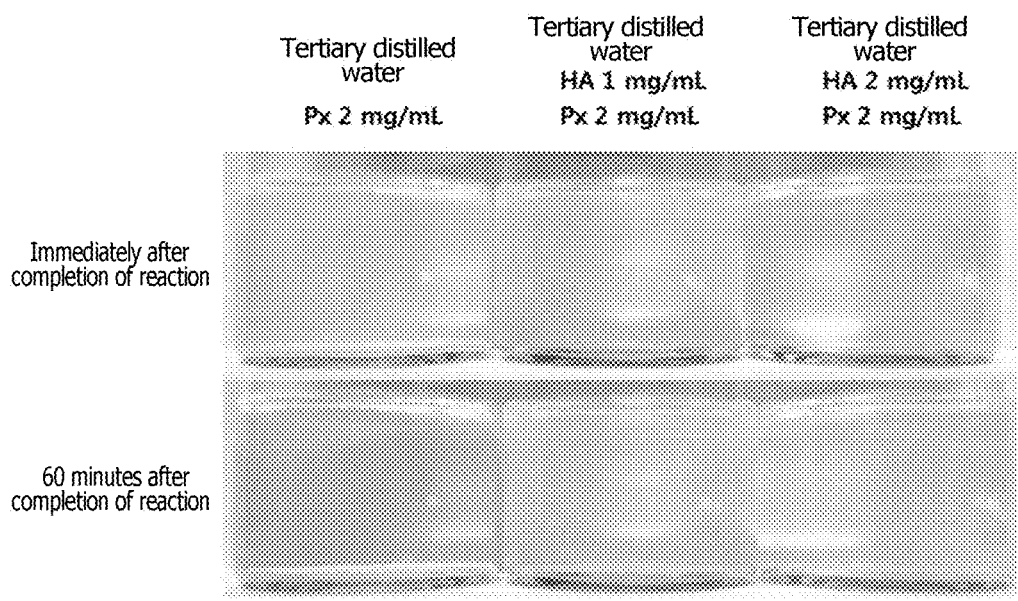
[FIG. 1B]
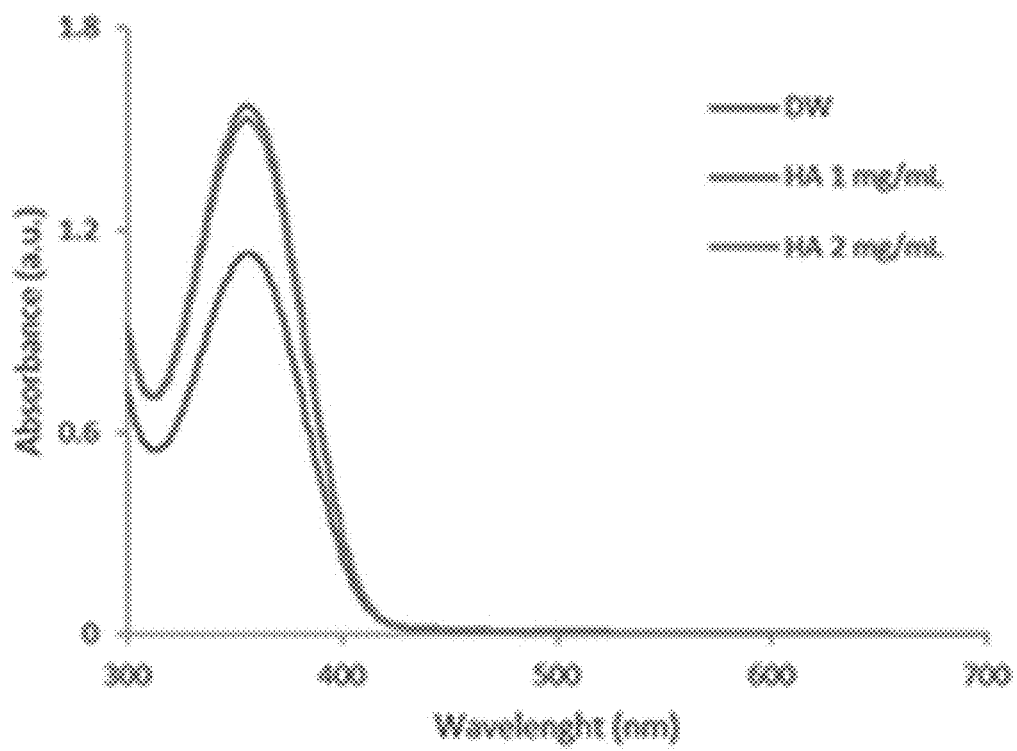

[FIG. 2]
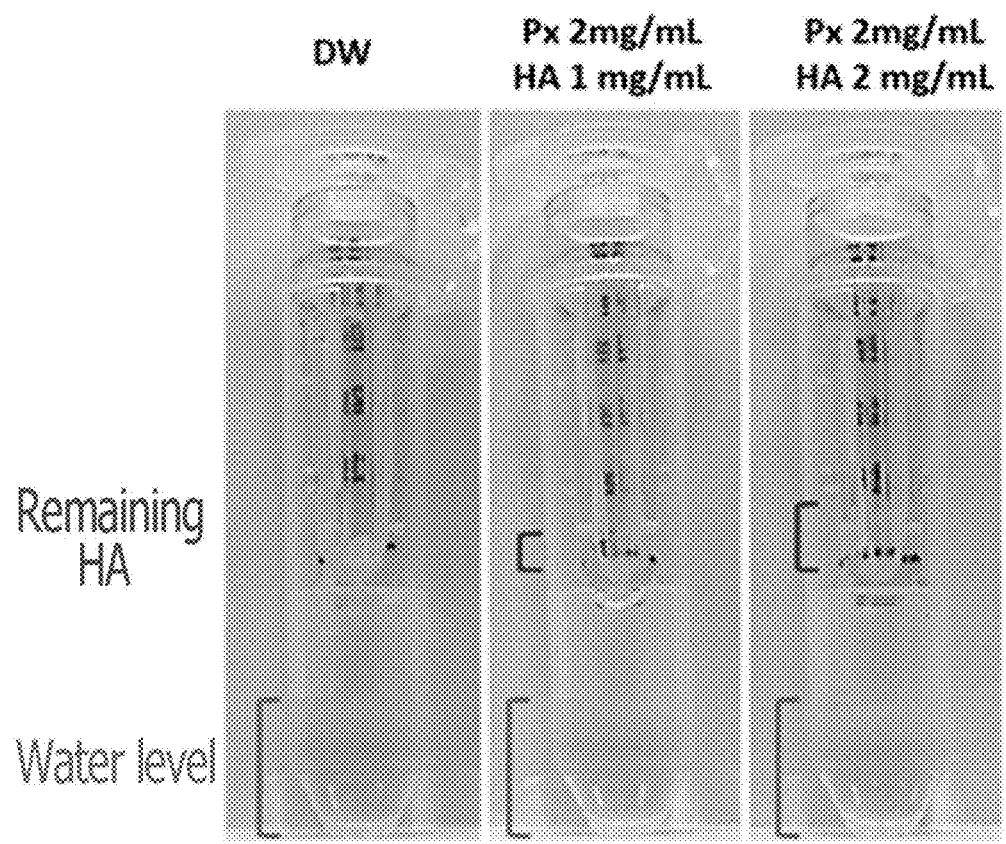

[FIG. 3]
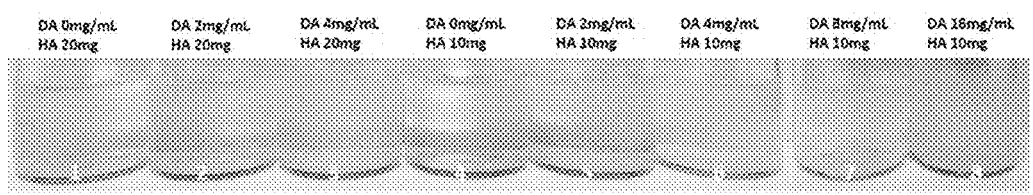
[FIG. 4]
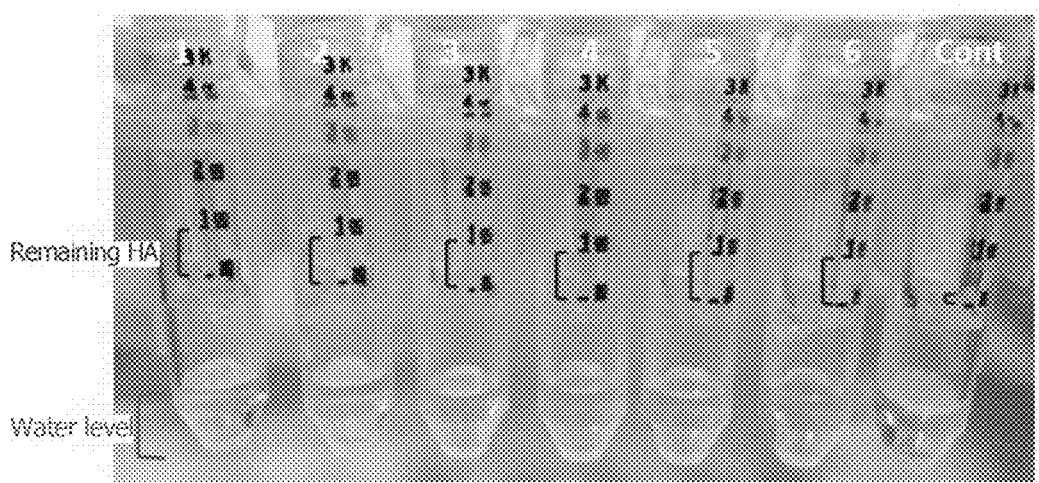

[FIG. 5A]
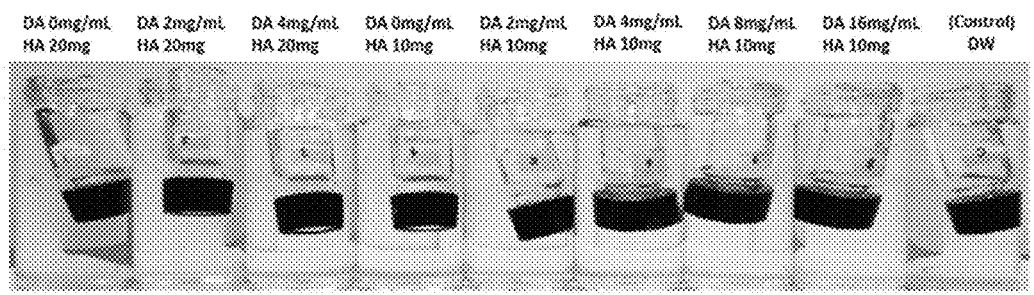
[FIG. 5B]
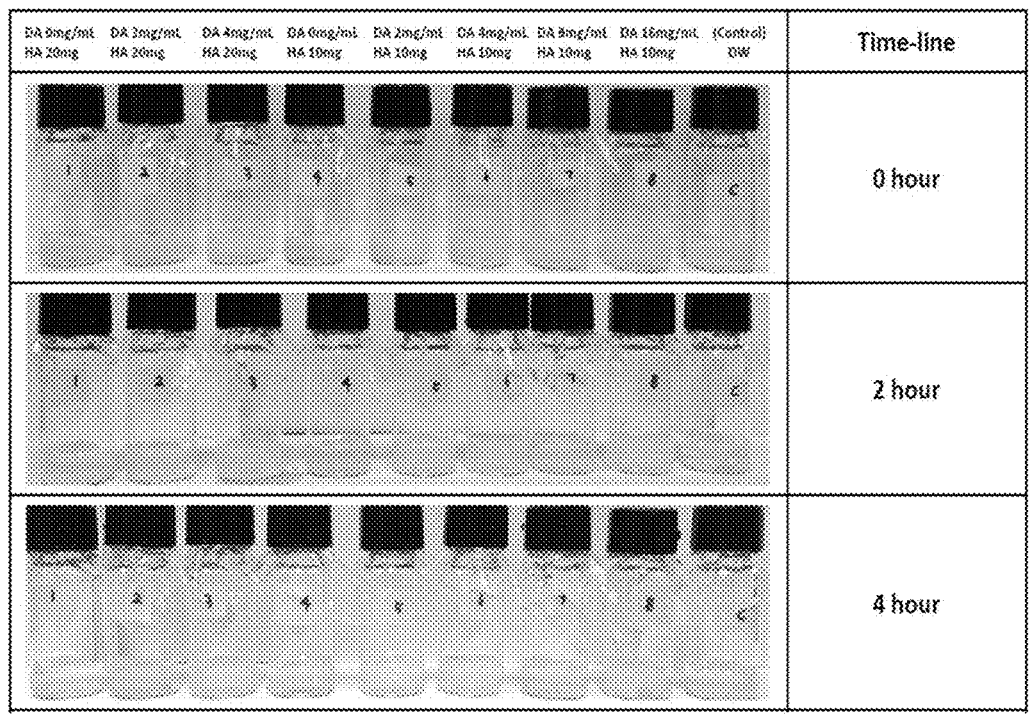

[FIG. 6]
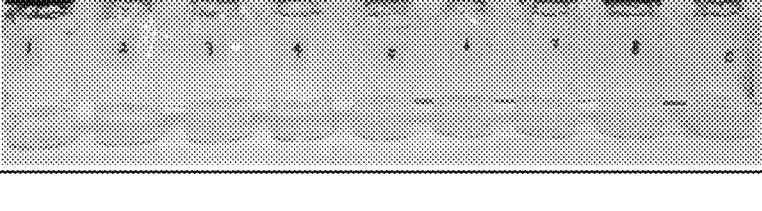
[FIG. 7]
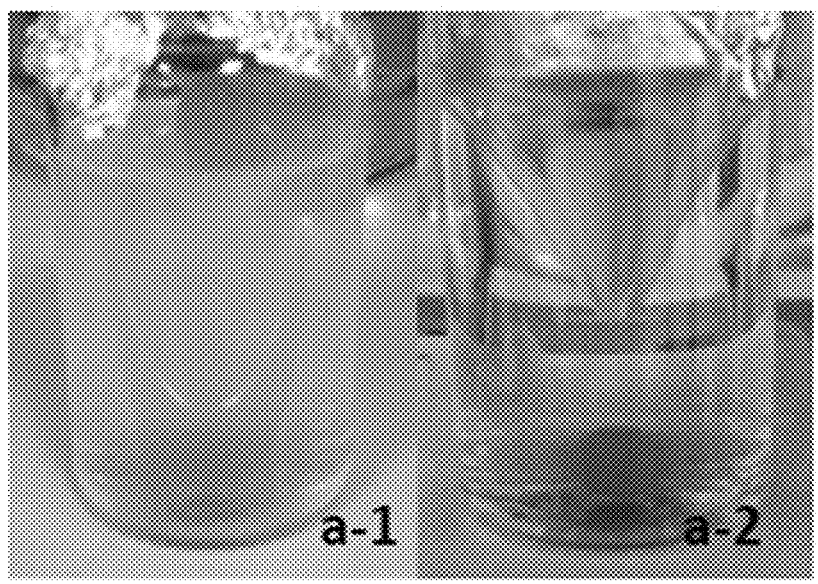

[FIG. 8]
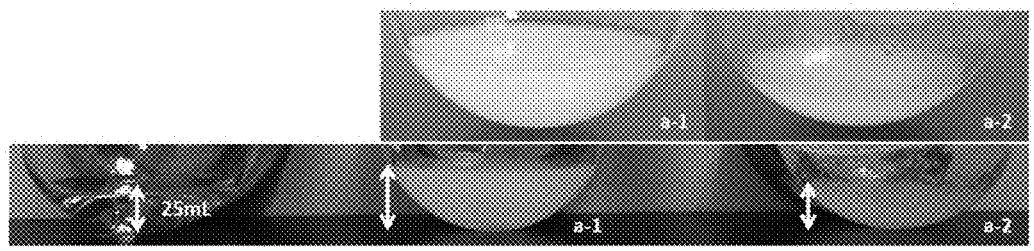
[FIG. 9]
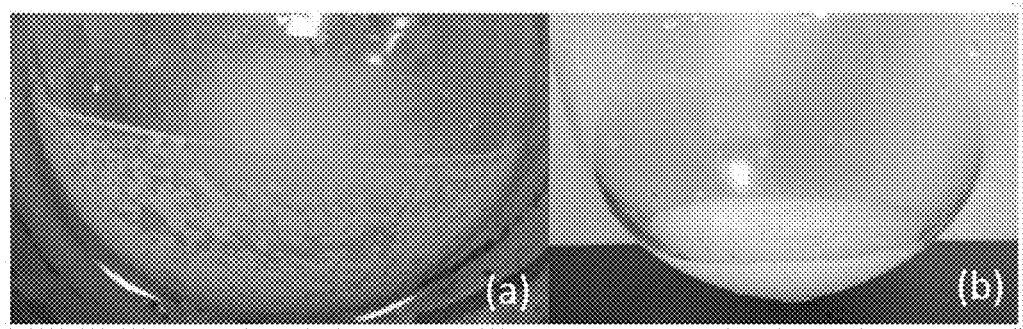
[FIG. 10]
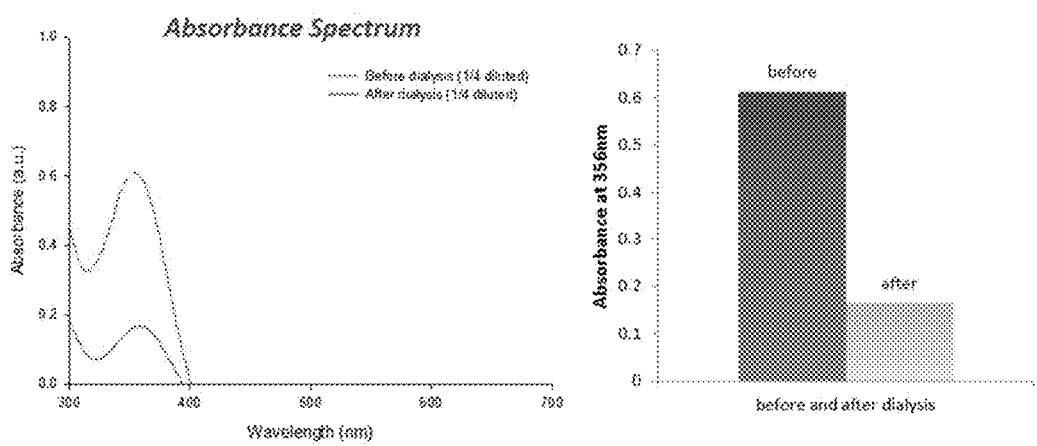

[FIG. 11]
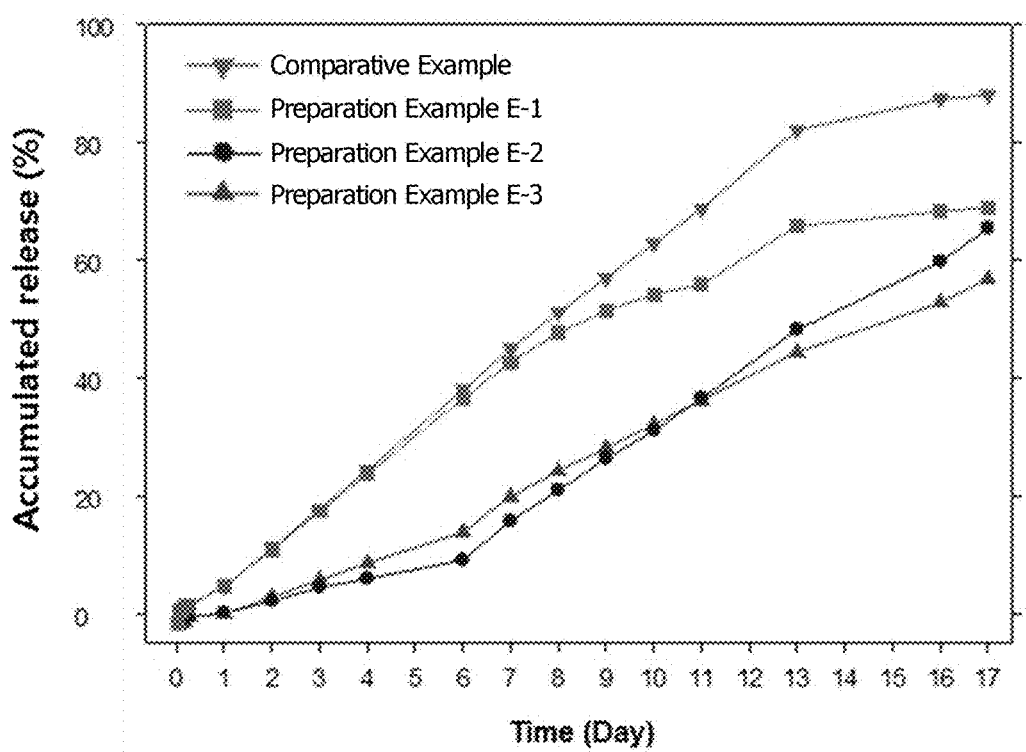

SUSTAINED-RELEASE PREPARATION OF POORLY SOLUBLE DRUG

TECHNICAL FIELD

The present invention relates to a pharmaceutical composition including a poorly soluble drug, hyaluronic acid, and a fatty acid and a method of preparing the same.

BACKGROUND ART

The prevalence of arthritis has been increased gradually with an aging society, and the treatment and management of arthritis directly affect the quality of life of patients. In fact, the domestic prevalence of osteoarthritis over the age of 50 in 2010-2013 was overall 12.5% (5.1% for males and 18.9% for females), and the prevalence of osteoarthritis appears to increase with age. According to the current status of management of osteoarthritis, only 64.6% of the total osteoarthritis cases were diagnosed, and only about half of them were cured, showing that the disease becomes chronic with age (national health statistics, 2013; Korea Centers for Disease Control and Prevention of the Ministry of Health and Welfare). Therefore, the social demand for the development of novel drugs for treating arthritis and alleviating symptoms seems to continuously increase.

Polymeric hyaluronic acid or a pharmaceutically acceptable salt thereof has been used as a therapeutic agent for degenerative arthritis, rheumatoid arthritis, or the like. The hyaluronic acid or the pharmaceutically acceptable salt thereof is conventionally formulated into liquid injections to be directly administered to an affected area such as the joint of a knee, a shoulder, or the like, and it has been reported that the hyaluronic acid or the pharmaceutically acceptable salt thereof, which is a viscoelastic polymer substance, is also directly injected into the articular cavity to reduce the impact caused by the loss of cartilage tissue in a patient with arthritis during joint movement and to help a lubrication action, by which dysfunction caused by arthritis is improved and joint pain is suppressed as well as alleviating joint pain and normalizing a function of joint.

Meanwhile, a poorly soluble drug has problems of low solubility, poor releasability in the body, and the like, and thus efforts to improve the solubility and release behavior of a poorly soluble drug have been continuously made. A nonsteroidal anti-inflammatory drug (NSAID), which is one of poorly soluble drugs, generally refers to all types of drugs that are not steroids in terms of structure and are used for pyrexia, pain, inflammation, and the like, and has currently been used to treat degenerative arthritis due to its excellent analgesic and antiphlogistic actions and long half-life in blood. Particularly, piroxicam, which is one of the NSAIDs, has been proven to have excellent local anti-inflammatory and analgesic actions and also reported to effectively remove inflammation when directly administered to the articular cavity of arthroscopic surgery patients.

In addition, it was confirmed that when hyaluronic acid is administered in combination with some NSAIDs to the articular cavity, the effect of hyaluronic acid injections can be improved.

However, when a hyaluronic acid/NSAID is administered as an injection, there is a problem in which a pharmacological activity is decreased due to a decrease in molecular size and viscosity caused by the reduction-oxidation and a series of hydrolysis of hyaluronic acid, and piroxicam is precipitated (Korean Unexamined Patent Publication No. 1994-0001891).

Therefore, there is a need of novel formulation of a hyaluronic acid/NSAID having excellent stability and capable of maintaining a pharmacological activity for a long period.

DISCLOSURE

Technical Problem

The present application is designed to solve the aforementioned problems and is directed to providing a pharmaceutical composition of a poorly soluble drug, which has excellent stability and is capable of sustainedly releasing the drug, and a method of preparing the same.

Technical Solution

In order to accomplish the above objective, the present invention provides a pharmaceutical composition including a poorly soluble drug or a pharmaceutically acceptable salt thereof; hyaluronic acid or a pharmaceutically acceptable salt thereof; and a C8 to C26 fatty acid.

In addition, the present invention provides a method of preparing a pharmaceutical composition, which includes mixing a solution prepared by dissolving a poorly soluble drug or a pharmaceutically acceptable salt thereof and a C8 to C26 fatty acid in a solvent; and a hyaluronic acid aqueous solution.

Additionally, the present invention provides a pharmaceutical composition for antiphlogistic and analgesic effects, which includes a nonsteroidal anti-inflammatory drug or a pharmaceutically acceptable salt thereof; hyaluronic acid or a pharmaceutically acceptable salt thereof; and a C8 to C26 fatty acid.

In addition, the present invention provides a method of preparing a pharmaceutical composition for antiphlogistic and analgesic effects, which includes mixing a solution prepared by dissolving a nonsteroidal anti-inflammatory analgesic drug or a pharmaceutically acceptable salt thereof and a C8 to C26 fatty acid in a solvent; and a hyaluronic acid aqueous solution.

Advantageous Effects

A pharmaceutical composition according to the present application has excellent stability even when stored for a long period and is capable of sustainedly releasing the drug so that an overdose of the drug can be prevented and the therapeutic efficiency at an affected area can be improved.

DESCRIPTION OF DRAWINGS

The patent or application file contains at least one drawing executed in color. Copies of this patent or patent application publication with color drawing(s) will be provided by the Office upon request and payment of the necessary fee.

FIG. 1A shows the effect of a hyaluronic acid concentration in a composition according to an embodiment of the present invention, which was analyzed through visual observation.

FIG. 1B shows the effect of a hyaluronic acid concentration in a composition according to an embodiment of the present invention, which was analyzed based on an absorbance spectrum.

FIG. 2 shows the effect of a hyaluronic acid concentration in a composition according to an embodiment of the present invention, which was analyzed using a centrifugal filter.

FIG. 3 shows the effect of a fatty acid concentration in a composition according to an embodiment of the present invention, which was analyzed through visual observation. In FIG. 3, 1 is Comparative Example A, 2 is Preparation Example A-1, 3 is Preparation Example A-2, 4 is Comparative Example B, 5 is Preparation Example B-1, 6 is Preparation Example B-2, 7 is Preparation Example C, and 8 is Preparation Example D.

FIG. 4 shows the effect of a fatty acid concentration in a composition according to an embodiment of the present invention, which was analyzed using a centrifugal filter. In FIG. 4, 1 is Comparative Example A, 2 is Preparation Example A-1, 3 is Preparation Example A-2, 4 is Comparative Example B, 5 is Preparation Example B-1, and 6 is Preparation Example B-2.

FIG. 5A shows a process in which samples prepared according to conditions of a control, preparation examples, and comparative examples are input into membrane filters and then immersed in ultrapure water in a composition according to an embodiment of the present invention.

FIG. 5B shows the drug release behavior according to concentrations of a fatty acid and hyaluronic acid in a composition according to an embodiment of the present invention, which was determined over time (in hours).

FIG. 6 shows the drug release behavior according to concentrations of a fatty acid and hyaluronic acid in a composition according to an embodiment of the present invention, which was determined over time (in days).

FIG. 7 shows the effect of heating during stirring in the preparation of a composition according to an embodiment of the present invention.

FIG. 8 shows the effect of a temperature condition during stirring for evaporating methanol in the preparation of a composition according to an embodiment of the present invention.

FIG. 9 shows the evaporation of methanol and re-dispersion in the preparation of a composition with an optimum composition according to an embodiment of the present invention.

FIG. 10 shows the release behavior of piroxicam according to Preparation Example E-3, which was analyzed based on an absorbance spectrum.

FIG. 11 shows the release behavior of piroxicam, which was quantitatively analyzed based on an absorbance spectrum.

MODES OF THE INVENTION

The present invention provides a pharmaceutical composition including a poorly soluble drug or a pharmaceutically acceptable salt thereof; hyaluronic acid or a pharmaceutically acceptable salt thereof; and a C8 to C26 aliphatic hydrocarbon derivative.

In the present invention, hyaluronic acid and an aliphatic hydrocarbon derivative are added to a poorly soluble drug so that the release of the poorly soluble drug may be controlled and excellent stability and dispersibility may be maintained.

In one embodiment, the poorly soluble drug may be coenzyme Q10, ursodeoxycholic acid, ilaprazole, paclitaxel, or imatinib mesylate.

In one embodiment, the poorly soluble drug may be a nonsteroidal anti-inflammatory drug (NSAID). A pharmaceutical composition including a NSAID may be used for antiphlogistic and analgesic purposes.

In the present invention, hyaluronic acid and an aliphatic hydrocarbon derivative are added to a NSAID so that the release of a NSAID may be controlled and excellent stability and dispersibility may be maintained. In one embodiment, the NSAID generally refers to all types of drugs that do not include steroids and act for antiphlogistic and analgesic effects, and the type thereof is not particularly limited. For example, the anti-inflammatory drug may be one or more selected from the group consisting of aspirin, diflunisal, salicylic acid, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, mefenamic acid, meclofenamic acid, flufenamic acid, tolfenamic acid, celecoxib, rofecoxib, valdecoxib, parecoxib, lumiracoxib, etoricoxib, firocoxib, nimesulide, clonixin, and licofelone. More specifically, the anti-inflammatory drug may be piroxicam.

In the present invention, the pharmaceutically acceptable salt of the poorly soluble drug refers to an organic or inorganic addition salt at a concentration such that it exhibits an effective action relatively nontoxic and harmless to patients and side effects caused by this salt do not impair the advantageous efficacy of the poorly soluble drug. For example, the pharmaceutically acceptable salt thereof may be an acid addition salt formed of an organic acid or an inorganic acid. The organic acid includes, for example, a formic acid-, acetic acid-, propionic acid-, lactic acid-, butyric acid-, isobutyric acid-, trifluoroacetic acid-, malic acid-, maleic acid-, malonic acid-, fumaric acid-, succinic acid-, succinamic acid-, glutamic acid-, tartaric acid-, oxalic acid-, citric acid-, glycolic acid-, glucuronic acid-, ascorbic acid-, benzoic acid-, phthalic acid-, salicylic acid-, anthranilic acid-, dichloroacetic acid-, aminooxyacetic acid-, benzenesulfonic acid-, p-toluenesulfonic acid-, or methanesulfonic acid-based salt. The inorganic acid includes, for example, a hydrochloric acid-, bromic acid-, sulfuric acid-, phosphoric acid-, nitric acid-, carbonic acid-, and boric acid-based salt, and is preferably in the form of a hydrochloride or an acetate. Also, the pharmaceutically acceptable salt thereof may be alkali metal salts (sodium salts, potassium salts, etc.), alkaline earth metal salts (calcium salts, magnesium salts), or the like.

In the present invention, the hyaluronic acid includes a hyaluronic acid derivative, a hyaluronate, a mixture including hyaluronic acid, and the like as well as hyaluronic acid itself. The hyaluronate may be an organic salt or an inorganic salt. Examples of the inorganic hyaluronate include sodium hyaluronate, magnesium hyaluronate, zinc hyaluronate, cobalt hyaluronate, and the like, and examples of the organic hyaluronate include tetrabutylammonium hyaluronate and the like. In the present invention, the molecular weight of hyaluronic acid is not particularly limited, and may be, for example, 500,000 to 10,000,000 or 1,000,000 to 3,000,000.

In the present invention, the aliphatic hydrocarbon derivative may be one or more selected from the group consisting of a fatty acid, a fatty amine, a fatty sulfonic acid, and a fatty alcohol. Therefore, the C8 to C26 aliphatic hydrocarbon derivative may be one or more selected from the group consisting of a C8 to C26 fatty acid, a C8 to C26 fatty amine, a C8 to C26 fatty sulfonic acid, and a C8 to C26 fatty alcohol.

In one embodiment, the C8 to C26 fatty acid may be one or more selected from the group consisting of myristoleic acid, palmitoleic acid, sapienic acid, oleic acid, elaidic acid, vaccenic acid, linoleic acid, linolenic acid, linoelaidic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, and cerotic acid.

In one embodiment, the C8 to C26 fatty amine may be one or more selected from the group consisting of decyl dimethyl amine, dodecyl dimethyl amine, tetradecyl dimethyl amine, hexadecyl dimethyl amine, octadecyl dimethyl amine, palmityl amine, palmitoleyl dimethyl amine, oleyl dimethyl amine, eicosyl dimethyl amine, myristoleyl dimethyl amine, dodecyl amine, tetradecyl amine, myristoleyl amine, hexadecyl amine, palmitoleyl amine, octadecyl amine, oleyl amine, eicosyl amine, docosyl amine, octyl amine, decyl amine, dimethyl elaidyl amine, linoleyl amine, arachidyl behenyl amine, erucyl amine, capryl amine, dimethyl myristyl amine, stearyl amine, arachidonoyl amine, and behenyl dimethyl amine.

In one embodiment, the C8 to C26 fatty sulfonic acid or a salt thereof may be one or more selected from the group consisting of myristoleyl methane sulfate, sodium palmityl sulfate, sodium oleyl sulfate, sodium elaidyl sulfate, elaidyl methane sulfate, vaccenyl methane sulfate, linoleyl methane sulfate, linoelaidyl methane sulfate, arachidyl sulfate sodium, erucyl methane sulfate, docosahexaenoyl methane sulfate, sodium capryl sulfate, sodium lauryl sulfate, sodium myristyl sulfate, sodium palmityl sulfate, sodium stearyl sulfate, sodium arachidyl sulfate, and sodium behenyl sulfate.

In one embodiment, the C8 to C26 fatty alcohol may be one or more selected from the group consisting of myristoleyl alcohol, oleyl alcohol, cis-vaccenyl alcohol, linoleyl alcohol, trans-linoelaidyl alcohol, arachidyl alcohol, erucyl alcohol, docosahexaenoyl alcohol, capryl alcohol, lauryl alcohol, myristyl alcohol, palmitoleyl alcohol, stearyl alcohol, arachidyl alcohol, behenyl alcohol, lignoceric alcohol, and cerotyl alcohol.

In one embodiment, the poorly soluble drug or the pharmaceutically acceptable salt thereof, the hyaluronic acid or the pharmaceutically acceptable salt thereof, and the C8 to C26 aliphatic hydrocarbon derivative may be included at 1 to 10 parts by weight, 7 to 70 parts by weight, and 14 to 140 parts by weight, respectively. Within the above ranges, the drug may exhibit excellent dispersibility and stability, and simultaneously the release thereof may be controlled. For example, a sustained release of the drug may be induced within the above ranges. Also, when the content of hyaluronic acid is within the above range, a pain-relieving function of hyaluronic acid itself may be expected.

The pharmaceutical composition according to an embodiment of the present invention may include a pharmaceutically acceptable carrier, an excipient, a stabilizer, an additive, or the like. The pharmaceutically acceptable carrier may contain various components such as a buffer solution, injectable sterile water, general saline or phosphate-buffered saline, sucrose, histidine, polysorbates, and the like. As the excipient, dextrins, cyclodextrin, polyethylene glycol, or derivatives thereof are included.

A formulation of the pharmaceutical composition according to an embodiment of the present invention is not particularly limited. The pharmaceutical composition according to the present invention may be formulated into a formulation for parenteral administration, sterilized aqueous solutions, non-aqueous solvents, suspensions, emulsions, lyophilized formulations, or the like. For example, the pharmaceutical composition may be a gel or injectable formulation. For example, when the poorly soluble drug is a NSAID, hyaluronic acid loaded with an aliphatic hydrocarbon derivative as an excipient and a NSAID as an effective ingredient is formulated into a gel form, and thus the aliphatic hydrocarbon derivative/NSAID/hyaluronic acid gel may be directly injected into the articular cavity to effectively treat, improve, or prevent arthritis.

Therefore, the pharmaceutical composition according to an embodiment of the present invention may be used for the purpose of treating or preventing arthritis or inflammatory diseases. For example, the pharmaceutical composition may be used for osteoarthritis, rheumatoid arthritis, moderate pain caused by inflammation and tissue damage, inflammatory arthropathy, tennis elbow, acute gout, or the like. Also, the pharmaceutical composition according to another embodiment of the present invention may be used for the purpose of treating coenzyme Q10 deficiency, hypertension, liver diseases, ulcers, cancer, or leukemia.

In addition, the present invention provides a method of preparing a pharmaceutical composition, which includes mixing a solution prepared by dissolving a poorly soluble drug or a pharmaceutically acceptable salt thereof and a C8 to C26 aliphatic hydrocarbon derivative in a solvent; and a hyaluronic acid aqueous solution. Specifically, a pharmaceutical composition may be prepared by dissolving a poorly soluble drug or a salt thereof and an aliphatic hydrocarbon derivative in a solvent to prepare a poorly soluble drug solution; dissolving hyaluronic acid in water to prepare a hyaluronic acid aqueous solution; and then bringing the two solutions in contact.

In one embodiment, the poorly soluble drug may be a NSAID. All the contents regarding a NSAID described above may be equally applied.

In one embodiment, the solvent may be dimethyl sulfoxide, dimethylformamide, dimethylacetamide, N-methyl-2-pyrrolidone, pyrrolidone, 1,3-dimethyl-3,4,5, 6-tetrahydro-2(1H)-pyrimidinone, hexamethylphosphoramide, chloroform, dichloromethane, 1,4-dioxane, acetone, acetic acid, n-methyl-2-pyrrolidone, dimethyl sulfoxide, or methanol.

In one embodiment, the mixing may be carried out by adding the solution prepared by dissolving a poorly soluble drug or a pharmaceutically acceptable salt thereof and a C8 to C26 aliphatic hydrocarbon derivative in a solvent dropwise to the hyaluronic acid aqueous solution.

In one embodiment, the mixing may be carried out at 44 to 45° C. Within the above temperature range, the hyaluronic acid, the poorly soluble drug, and the aliphatic hydrocarbon derivative may be uniformly mixed without deterioration of the components.

According to an embodiment of the present invention, the method of preparing a pharmaceutical composition may further include stirring the mixture at 30 to 35° C. after the mixing. By carrying out the stirring within the above temperature range, the solvent may be evaporated at an appropriately rate and removed, and the pharmaceutical composition may be formulated into a form of a particle in which hyaluronic acid is present on a surface thereof. Also, by carrying out the stirring within the above temperature range, the dispersibility and stability of the drug may be improved. When the stirring is carried out at high temperature out of the above temperature range, the solvent is rapidly evaporated so that particles are not uniformly produced.

BEST MODE

Hereinafter, the present invention will be described in detail with reference to examples of the present application.

However, the following examples are only exemplary and the scope of the present application is not limited to the following examples.

[Preparation Example 1] Preparation of Composition Including Hyaluronic Acid (HA), Piroxicam (PX), and Fatty Acid (FA)

A hyaluronic acid gel preparation including a fatty acid and loaded with piroxicam was prepared through nanoprecipitation. First, HA was dispersed in distilled water (DW) to prepare a HA aqueous solution. PX and a FA were dispersed in 1 ml of methanol at temperatures above a melting point of the FA to prepare a PX-FA solution. The HA aqueous solution and the PX-FA solution were mixed, secondarily stirred at 30 to 35° C. and concentrated under reduced pressure using a vacuum concentrator and stirrer to prepare a composition including HA, a FA, and PX. The composition of each of Preparation Examples and Comparative Examples is shown in the following Table 1. Dodecanoic acid (DA) was used as a fatty acid.

TABLE 1

| | PX content (mg/ml) | FA content (mg/ml) | HA content (nag) | DW content (ml) |
|---|---|---|---|---|
| Comparative Example A | 2 | 0 | 20 | 10 |
| Preparation Example A-1 | 2 | 2 | 20 | 10 |
| Preparation Example A-2 | 2 | 4 | 20 | 10 |
| Comparative Example B | 2 | 0 | 10 | 10 |
| Preparation Example B-1 | 2 | 2 | 10 | 10 |
| Preparation Example B-2 | 2 | 4 | 10 | 10 |
| Preparation Example C | 2 | 8 | 10 | 10 |
| Preparation Example D | 2 | 16 | 10 | 10 |

[Experimental Example 1-1] Evaluation of Stability of Hyaluronic Acid (HA)/Piroxicam (PX) Preparation According to HA Concentration A hyaluronic acid gel preparation loaded with piroxicam was prepared through nanoprecipitation. HA was dispersed in water at varying concentrations (1 mg/ml, 2 mg/ml) to prepare 10 ml of a HA aqueous solution. 1 ml of PX was dispersed at 2 mg/ml in methanol to prepare a PX solution. The PX solution was added to the HA aqueous solution and then stirred for 8 hours to prepare a HA gel loaded with PX. As a control, 10 ml of distilled water (DW) including PX dispersed therein was used.

An experiment for evaluating the dispersibility of each solution after the completion of the reaction was carried out.

(1) The dispersibility of each solution was evaluated immediately after the completion of the reaction and 60 minutes after the completion of the reaction, through visual observation and based on an absorbance spectrum.

As a result, as shown in FIG. 1A, it can be confirmed that dispersibility increased in proportion to the concentration of HA. In the solution including HA at 2 mg/ml, particles were uniformly distributed, and thus the best dispersibility was exhibited. This means that as the concentration of HA is higher, the dispersibility of a preparation is improved. Also, it can be confirmed that 60 minutes after the completion of the reaction, particles had settled on a bottom in the case of a control (DW), and a smaller amount of particles than that in a control had settled on a bottom in the case of the solution including HA at 1 mg/ml. That is, this result means that the dispersibility of a preparation is improved in proportion to the concentration of HA.

(2) In addition, the absorbance spectrum of each solution after the completion of the reaction was analyzed (at a wavelength of 300 nm to 700 nm). Piroxicam exhibits a strong peak at 356 nm.

As a result, as shown in FIG. 1B, it can be seen that a control exhibited a lowered absorbance due to precipitation of PX, and the two solutions including HA exhibited absorbance peaks similar to each other. This means that the dispersibility of PX is improved by including HA.

(3) In addition, each solution after the completion of the reaction was subjected to spinning down using a centrifugal filter having a molecular weight cut-off of 3 kDa.

As a result, as shown in FIG. 2, it can be confirmed that 20 minutes after the spinning down, DW was completely separated, leaving only PX, in the control, whereas in solutions including HA, a state in which PX was dispersed in HA was maintained.

[Experimental Example 1-2] Evaluation of Stability of Hyaluronic Acid (HA)/Piroxicam (PX) Preparation According to Fatty Acid (FA) Content The dispersibility of each solution was evaluated in the same manner as in (1) to (3) of Experimental Example 1-1. Dodecanoic acid (DA) was used as a FA.

(1) As a result, as shown in FIG. 3, in the case of Comparative Examples A and B not including DA, particles with a smaller size were distributed compared to Preparation Examples. Also, in the case of Preparation Examples including DA, particles with a larger size than that in Comparative Examples A and B were formed and were more agglomerated as a content of DA increased. This suggests that a higher content of DA results in a larger size of particles and thus a lower release rate of PX.

In addition, it can be confirmed that a larger number of particles had not settled but were dispersed in the case of Preparation Examples A-1 and A-2 including a larger amount of HA compared to Preparation Examples B-1 and B-2 including a smaller amount of HA. This means that as a concentration of HA is higher, the dispersibility of PX is improved.

(2) As a result of filtration using a centrifugal filter having a molecular weight cut-off of 3 kDa, as shown in FIG. 4, it can be seen that when a solution prepared by dissolving PX in methanol, which is a control, was subjected to centrifugal filtration, most of the solution including PX dissolved therein passed through a filtration membrane, whereas in the case of the experimental groups, only DW passed through a filtration membrane of the centrifugal filter, leaving both HA and PX unfiltered, indicating that PX is not dispersed in DW and attains dispersibility in an aqueous solution due to HA.

[Experimental Example 1-3] Determination of PX Release Behavior According to Concentrations of Dodecanoic Acid (DA) and Hyaluronic Acid (HA)

(1) The PX release behaviors of Preparation Examples and Comparative Examples according to Preparation Example 1 were determined using a membrane filter having molecular weight cut-off of 3 kDa. As a control, a 2 mg/ml PX solution prepared by diluting PX in 10 ml of DW was used. 2 mL of each of the samples prepared according to conditions of a control, Preparation Examples, and Comparative Examples was taken out and introduced into a membrane filter, and then the membrane filter was immersed in ultrapure water (FIG. 5A). The extent of a drug release before the immersion and at 2 and 4 hours of the immersion was determined, and the extent of a drug release on Day 1, Day 5, and Day 7 of the immersion was also identified.

As a result, as shown in FIG. 5B, there was no significant difference in drug release for 4 hours, except for a control.

However, as shown in FIG. 6, it can be confirmed based on observation by Day 7 that the drug was most slowly released in the case of Preparation Example A-2. Also, it can be confirmed that there was no significant difference in the extent of drug release according to a content of DA in Preparation Examples C and D.

This means that a drug release rate may be adjusted according to contents of DA and HA, and PX is most slowly released when a large amount of HA and 2 to 6 mg/ml of DA are included.

[Preparation Example 2] Design of Preparation of Clinical-Scale Composition Including Hyaluronic Acid (HA), Piroxicam (PX), and Fatty Acid (FA) which is Administrable Once a Week The pharmaceutical composition according to the present invention is aimed at having a dosing period of at most once per week. Accordingly, the optimum formulation conditions were established in consideration of the results of Experimental Examples 1-1 to 1-3 and the dose of commercially available HA and PX preparations. The acceptable daily dose of a commercially available PX preparation is 20 mg, and the acceptable daily dose of a commercially available HA preparation is 20 mg/2 ml. Therefore, the pharmaceutical composition was designed to include 20 mg/2 ml of HA and the maximum dose, 140 mg (2 mg/ml), of PX in the total composition. In this case, dodecanoic acid (DA) was included at a content of 280 mg (4 mg/ml).

In order to prepare a composition with the desired contents, the specific optimum preparation conditions were established. Specifically, 140 mg of PX and 280 mg of DA were dissolved in 70 ml of methanol to prepare a PX solution. 50 mg of HA was dissolved in 25 ml of distilled water (DW) to prepare a HA aqueous solution. Then, the PX solution was added dropwise to the HA aqueous solution.

(1) After the dropwise addition was completed, the resulting mixture was stirred for 24 hours, while raising or not raising a temperature up to 45° C. so as to set a temperature condition for forming a uniform mixture.

As a result, as shown in FIG. 7, there was no difference in volume according to whether or not a temperature was raised, but when the temperature was raised (a-2), HA, PX, and DA were completely dissolved to exhibit a transparent appearance as compared with when the temperature was not raised (a-1). However, if the temperature is raised to greater than 45° C., each material is likely to be deteriorated. Therefore, the stirring temperature was set so as not to exceed 45° C.

(2) Afterward, the mixture was subjected to rotary evaporation using a rotary evaporator for 1.5 hours to evaporate methanol. The rotary evaporation was carried out while heating the mixture in boiling water using a water bath kept to 40° C. (a-2 of FIG. 8) or not heating the mixture (a-1 of FIG. 8) for comparison.

As a result, as shown in FIG. 8, it can be seen that in the case where a temperature was not raised (a-1), methanol remained even after the rotary evaporation and thus the volume was maintained to be about 35 ml, whereas in the case where the stirring was carried out while raising a temperature (a-2), methanol was completely evaporated and thus PX was dried and precipitated. Therefore, it can be seen that there is a need for raising a temperature above a predetermined temperature so that methanol can be evaporated, and it is important to set an appropriate temperature range to prevent PX from being excessively precipitated.

(3) Accordingly, the rotary evaporation was carried out at varying temperatures (30° C. and 44° C.) to set an optimum temperature range for evaporating methanol and simultaneously preventing PX from being excessively precipitated.

As a result, as shown in FIG. 9, it can be seen that when methanol was evaporated in a 30° C. bath using a rotary evaporator for 24 hours, methanol was more slowly evaporated as compared to when methanol was evaporated at 44° C. Also, it can be seen that when methanol was completely evaporated at 30° C. and a predetermined period of time had elapsed thereafter, a yellow HA-DA-PX preparation was precipitated on the wall of a container (FIG. 9(a)), and that the precipitated preparation was easily dispersed again in water using an ultrasonic generator (FIG. 9(b)). This result indicates that the heating at 40° C. or more during the preparation of the composition causes excessive evaporation of methanol to interfere with the preparation of the composition, and when methanol is evaporated, particularly, at 30 to 35° C., PX is not precipitated from the prepared composition so that it is possible to prevent unwanted loss of PX, and excellent re-dispersibility is exhibited. The composition of each of Preparation Examples and Comparative Example is shown in the following Table 2. Dodecanoic acid (DA) was used as a fatty acid.

TABLE 2

| | PX content (mg/ml) | FA content (mg/ml) | HA content (mg) | Buffer content (ml) |
|---|---|---|---|---|
| Comparative Example E | 140 | 0 | 0 | 2 |
| Preparation Example E-1 | 140 | 0 | 20 | 2 |
| Preparation Example E-2 | 140 | 280 | 20 | 2 |
| Preparation Example E-3 | 140 | 280 | 20 | 2 |

[Experimental Example 2-1] Determination of Drug Release Behavior

In the same composition as in Preparation Example 2, 140 mg of PX (2 mg/ml) and 280 mg of DA (4 mg/ml) were dispersed in 70 ml of methanol to prepare a PX solution, and 50 mg of HA was dissolved in 25 ml of DW to prepare a HA aqueous solution. The PX solution and the HA aqueous solution were mixed by adding the PX solution dropwise to the HA aqueous solution and stirred at 45° C. for 2 hours. Methanol was evaporated using a rotary evaporator (in a 30° C. bath) for 24 hours. After the evaporation of methanol using a rotary evaporator was completed, a yellow HA-DA-PX preparation was precipitated on the wall of a container, and the precipitated preparation was dispersed again in water using an ultrasonic generator. The preparation dispersed in water was freeze-dried at −80° C. and 0.004 bar for 24 hours to obtain yellow powder. The powder was ground and then dispersed in saline to prepare a HA-DA-PX preparation. The drug release behavior by Day 7 was identified through absorbance spectrum analysis using a membrane filter having molecular weight cut-off of 3 kDa. As a result, as shown in FIG. 10, it can be confirmed that after 7 days had elapsed, about 26% of PX remained with respect to an initial amount of PX.

This means that the PX preparation according to the present invention includes DA and HA so that it is possible to control the release of PX and sustain a pharmacological effect for a long period of one week or more.

[Experimental Example 2-2] Quantitative Analysis of Drug Release Behavior (1) 140 mg of PX was dispersed in 2 ml of a buffer to prepare a PX solution [Comparative Example E].

(2) 140 mg of PX (2 mg/ml) was dispersed in 70 ml of methanol to prepare a PX solution, and 20 mg of HA was dissolved in 50 ml of DW to prepare a HA aqueous solution. The PX solution and the HA aqueous solution were mixed by adding the PX solution dropwise to the HA aqueous solution, and methanol was evaporated using a rotary evaporator (in a 30° C. bath). After the evaporation of methanol using a rotary evaporator was completed, a yellow PX-HA preparation was precipitated on the wall of a container, and the precipitated preparation was dispersed again in water using an ultrasonic generator. The preparation dispersed in water was freeze-dried at −80° C. and 0.004 bar for 24 hours to obtain yellow powder. The powder was ground and then 40 mg (160 mg of PX-HA/4) thereof was taken out to be dispersed in 0.5 ml of a buffer to prepare a PX-HA preparation [Preparation Example E-1].

(3) 140 mg of PX (2 mg/ml) and 280 mg of DA (4 mg/ml) were dispersed in 70 ml of methanol to prepare a PX-DA solution, and 50 ml of a DW solution and a HA solution prepared by dissolving 20 mg of HA in 2 ml of a buffer were prepared. The PX-DA solution and 50 ml of the DW solution were mixed by adding the PX-DA solution dropwise to the DW solution, and methanol was evaporated using a rotary evaporator (in a 30° C. bath). After the evaporation of methanol using a rotary evaporator was completed, a yellow PX-DA preparation was precipitated on the wall of a container, and the precipitated preparation was dispersed again in water using an ultrasonic generator. The preparation dispersed in water was freeze-dried to obtain PX-DA powder. Afterward, the powder was ground and then 105 mg (420 mg of PX-DA/4) thereof was taken out to be mixed with 0.5 ml of the HA solution to prepare a PX-DA/HA preparation [Preparation Example E-2].

(4) 140 mg of PX (2 mg/ml) and 280 mg of DA (4 mg/ml) were dispersed in 70 ml of methanol to prepare a PX-DA solution, and 20 mg of HA was dissolved in 50 ml of DW to prepare a HA solution. The PX-DA solution and 50 ml of the HA solution were mixed by adding the PX-DA solution dropwise to the HA solution, and methanol was evaporated using a rotary evaporator (in a 30° C. bath). After the evaporation of methanol using a rotary evaporator was completed, a yellow PX-DA-HA preparation was precipitated on the wall of a container, and the precipitated preparation was dispersed again in water using an ultrasonic generator. The preparation dispersed in water was freeze-dried at −80° C. and 0.004 bar for 24 hours to obtain yellow powder. The powder was ground and then 110 mg (440 mg of PX-DA-HA/4) thereof was taken out to be dispersed in 0.5 ml of a buffer to prepare a PX-DA preparation [Preparation Example E-3].

(5) Each of the preparations according to Comparative Example E and Preparation Examples E-1, E-2, and E-3 was dispersed in 4.5 mL of a buffer, and the drug release behavior of the preparation by Day 7 was analyzed through absorbance spectrum analysis using a membrane filter having molecular weight cut-off of 3.5 kDa.

As a result, as shown in FIG. 11, it can be seen that after 17 days had elapsed, the preparations according to Comparative Example E and Preparation Example E-1 hardly released the drug, but the preparations according to Preparation Examples E-2 and E-3 sustainedly released the drug.

INDUSTRIAL APPLICABILITY

A pharmaceutical composition according to the present invention has excellent stability even when stored for a long period and is capable of sustainedly releasing the drug so that an overdose of the drug can be prevented and the therapeutic efficiency at an affected area can be improved.

The invention claimed is:

1. A pharmaceutical composition comprising:
   piroxicam or a pharmaceutically acceptable salt thereof;
   hyaluronic acid or a pharmaceutically acceptable salt thereof; and
   a C8 to C26 aliphatic hydrocarbon derivative or a salt thereof,
   wherein the pharmaceutical composition is prepared by adding a solution comprising piroxicam or a pharmaceutically acceptable salt thereof and the C8 to C26 aliphatic hydrocarbon derivative dropwise to an aqueous solution of hyaluronic acid or a pharmaceutically acceptable salt thereof, wherein the C8 to C26 aliphatic hydrocarbon derivative is lauric acid or a salt thereof, and
   wherein the pharmaceutical composition is a sustained release gel.

2. The pharmaceutical composition of claim 1, wherein the piroxicam or the pharmaceutically acceptable salt thereof, the hyaluronic acid or the pharmaceutically acceptable salt thereof, and the lauric acid or the salt thereof are included at 1 to 10 parts by weight, 7 to 70 parts by weight, and 14 to 140 parts by weight, respectively.

3. The pharmaceutical composition of claim 1, wherein the sustained release gel is an injectable formulation.

4. The pharmaceutical composition of claim 1, which is for treating coenzyme Q10 deficiency, hypertension, liver diseases, ulcers, cancer, leukemia, arthritis, or inflammatory diseases.

5. A method of preparing a pharmaceutical composition, comprising mixing a solution prepared by dissolving piroxicam or a pharmaceutically acceptable salt thereof and lauric acid in a solvent; and a hyaluronic acid aqueous solution, wherein the mixing is carried out by adding the solution prepared by dissolving the piroxicam or a pharmaceutically acceptable salt thereof and lauric acid in a solvent dropwise to the aqueous solution of hyaluronic acid or a pharmaceutically acceptable salt thereof.

6. The method of claim 5, further comprising removing a portion of the solvent at 30° C. to 35° C. using a rotary evaporator.

* * * * *